(12) United States Patent
Anderson, Jr. et al.

(10) Patent No.: US 11,785,878 B2
(45) Date of Patent: Oct. 17, 2023

(54) SYSTEMS AND METHODS FOR TILLAGE OPTIMIZATION USING NON-INVASIVE MULTIMODAL SENSORS

(71) Applicant: GroundTruth Ag, Inc., Raleigh, NC (US)

(72) Inventors: John Richard Anderson, Jr., Raleigh, NC (US); Graham Hunter Bowers, Raleigh, NC (US); Jacob Samuel Lasky, Raleigh, NC (US); Christopher Casey Nobblitt, Durham, NC (US)

(73) Assignee: GroundTruth Ag, Inc., Arlington, VA (US)

( * ) Notice: Subject to any disclaimer, the term of this patent is extended or adjusted under 35 U.S.C. 154(b) by 647 days.

(21) Appl. No.: 16/800,235

(22) Filed: Feb. 25, 2020

(65) Prior Publication Data

US 2021/0105931 A1    Apr. 15, 2021

Related U.S. Application Data

(60) Provisional application No. 62/961,411, filed on Jan. 15, 2020, provisional application No. 62/853,625, filed on May 28, 2019.

(51) Int. Cl.
*A01B 79/00* (2006.01)
*G06N 3/08* (2023.01)
(Continued)

(52) U.S. Cl.
CPC ........... *A01B 79/005* (2013.01); *G01N 33/24* (2013.01); *G06N 3/04* (2013.01); *G06N 3/08* (2013.01);
(Continued)

(58) Field of Classification Search
CPC ..... A01B 79/005; A01B 47/00; A01B 63/002; A01B 79/02; G06F 16/26; G06F 16/25;
(Continued)

(56) References Cited

U.S. PATENT DOCUMENTS

| | | | |
|---|---|---|---|
| 2003/0066357 A1* | 4/2003 | Upadhyaya | G01N 3/58 73/818 |
| 2013/0248212 A1* | 9/2013 | Bassett | A01B 71/02 172/4 |

(Continued)

OTHER PUBLICATIONS

Raper et al., Article: "Sensing Hard Pan Depth With Ground-Penetrating Radar". Published by the American Society of Agricultural and Biological Engineers, St. Joseph, Michigan www.asabe.orgw.asabe.org Citation: Transactions ofthe ASAE. 33 (1): 0041-0046. (doi: 10.13031/2013.31291) @1990 (Year: 1990).*

*Primary Examiner* — Evan Aspinwall
(74) *Attorney, Agent, or Firm* — PADDA LAW GROUP

(57) ABSTRACT

Methods, systems and devices for determining optimized tillage of a soil area are provided. Operations include transmitting, using at least one sensor, a data set regarding a physical, chemical and/or biological aspect of the soil area. Operations include receiving, using at least one computing device, the data set regarding the physical, chemical and/or biological aspect of the soil area. The at least one computing device removes a set of redundant data and the at least one computing device enhances a set of data that is not the set of redundant data. Operations include generating a visualization of the set of data that is not redundant data. The data that is not redundant data provides a data set reflecting a soil compaction measurement within the soil area and the soil area is not deeper than 36 inches from a surface of the soil area.

18 Claims, 11 Drawing Sheets

(51) Int. Cl.
*G01N 33/24* (2006.01)
*G06N 3/04* (2023.01)
*G06F 16/26* (2019.01)

(52) U.S. Cl.
CPC ........ *G01N 2033/245* (2013.01); *G06F 16/26* (2019.01)

(58) Field of Classification Search
CPC ............ G01N 33/24; G01N 2033/245; G01N 2001/021; G01N 1/02; G06N 3/04; G06N 3/08; G06Q 50/02; A01G 25/167; G06V 10/82; G06V 20/17; G06V 20/188; G06T 2207/30188; G06T 7/0004; G06T 2207/10032; G06T 2207/30261; G06T 2207/30252; G16Y 10/05; A01D 41/127; A01D 91/04
USPC .................. 172/172, 1; 701/1, 409, 50, 533; 702/188; 707/E17.009, 736; 706/16, 12, 706/46
See application file for complete search history.

(56) References Cited

U.S. PATENT DOCUMENTS

| | | | |
|---|---|---|---|
| 2016/0247079 A1* | 8/2016 | Mewes | G06N 5/048 |
| 2018/0120133 A1* | 5/2018 | Blank | G01D 18/002 |
| 2021/0190754 A1* | 6/2021 | Stoller | A01B 49/06 |

* cited by examiner

SYSTEMS AND METHODS FOR TILLAGE OPTIMIZATION USING NON-INVASIVE MULTIMODAL SENSORS

CROSS REFERENCE TO RELATED APPLICATIONS

The present application claims domestic priority to U.S. Provisional Patent Application No. 62/853,625, filed on May 28, 2019 and U.S. Provisional Patent Application No. 62/961,411 filed on Jan. 15, 2020, the disclosures and content of which are incorporated by reference herein in their entirety

BACKGROUND

The present disclosure relates to soil management and health, and, in particular, to providing tillage optimization data and control.

Research within the agricultural community has shown that management of crop production may be optimized by taking into account spatial variations that often exist within a given farming field. For example, by varying the farm inputs applied to a field according to local conditions within the field, a farmer can optimize crop yield as a function of the inputs being applied while preventing or minimizing environmental damage. This management technique has become known as precision, site-specific, prescription or spatially-variable farming.

The management of a field using precision farming techniques requires the gathering and processing of data relating to site-specific characteristics of the field. Generally, site-specific input data is analyzed in real-time or off-line to generate a prescription map (e.g., global information systems (GIS) type database) including desired application or control rates of a farming input. A control system reads data from the prescription map and generates a control signal which is applied to a variable-rate controller for applying a farming input to the field at a rate that varies as a function of the location. The effect of the inputs may be analyzed by gathering site-specific soil compaction, yield, and moisture content data and correlating this data with farming inputs, thereby allowing a user to optimize the amounts and combinations of farming inputs applied to the field.

The spatially-variable characteristic data may be obtained by in situ measurements, remote sensing, or sensing during field operations. In-situ measurements typically involve taking a soil probe and analyzing the soil in a laboratory to determine nutrient data or soil condition data such as soil type or soil classification. Taking in-situ measurements, however, is labor intensive and, due to high sampling costs, provides only a limited number of data samples. Remote sensing may include taking aerial photographs or generating spectral images or maps from airborne or spaceborne multispectral sensors. Data from remote sensing, however, can be difficult to correlate with a precise location in a field or with a specific quantifiable characteristic of the field. Both in-situ measurements and remote sensing may require a user to conduct an airborne or ground-based survey of the field apart from normal field operations.

Spatially-variable characteristic data may also be acquired during normal field operations using appropriate sensors supported by a combine, tractor or other vehicle. A variety of characteristics may be sensed including soil properties (e.g., organic matter, fertility, nutrients, moisture content, compaction, topography or altitude), crop properties (e.g., height, moisture content or yield), and farming inputs applied to the field (e.g., fertilizers, herbicides, insecticides, seeds, cultural practices or tillage parameters and techniques used). Specifically, soil compaction may limit crop productivity by 10% to 15% alone and may be the result of heavy machinery that is used to produce crops compressing soil and causing hardpans. Hardpans may be dense areas a few inches below the soil surface and may restrict root growth and may prevent roots from reaching nutrients and/or moisture that are located deeper in the soil.

Additionally, natural soil formation processes may create dense soil layers that are referred to as fragipans and that occur deeper in the soil than hardpans. Like hardpans, fragipans may restrict root growth thus preventing roots from reaching nutrients and/or moisture that is in the subsoil.

Logging spatially-variable characteristic data, such as soil density, may be accomplished in several ways. A farmer may walk or drive a vehicle through a field and take measurements at a plurality of locations in the field. These measurements are recorded. Locations of the measurement sites may be determined by reference to a map of the field, or from an electronic positioning unit. This technique, however, produces data which is difficult to integrate into an electronic site-specific farming system since the recorded data must be manually transferred to a site-specific farming database. Further, a large sampling of measurements must be made to obtain a significant sample population.

The approaches described in the Background section could be pursued, but are not necessarily approaches that have been previously conceived or pursued. Therefore, unless otherwise indicated herein, the approaches described in the Background section are not prior art to the claims in this application and are not admitted to be prior art by inclusion in the Background section.

SUMMARY

Some embodiments herein are directed to systems that include a vehicle that is configured to travel over a soil area, a location device that is configured to provide geographic location data corresponding to the vehicle, at least one sensor that is caused to move above a surface of the soil area as the vehicle travels thereon and to generate data relating to a physical, chemical and/or biological characteristic of the soil corresponding to the soil area, and a computer that is communicatively coupled to the at least one sensor and to the location device, that is configured to receive the geographic location data and the data relating to the physical, chemical and/or biological characteristic of the soil, and to generate location associated data relating to the physical, chemical and/or biological characteristic of the soil corresponding to the soil area.

Some embodiments are directed to methods for determining optimized tillage of a soil area. Operations of such methods may include transmitting, using at least one sensor, a data set regarding a physical, chemical and/or biological aspect of the soil area, receiving, using at least one computing device, the data set regarding the physical, chemical and/or biological aspect of the soil area. In some embodiments, the at least one computing device removes a set of redundant data and enhances a set of data that is not the set of redundant data. Operations may include generating a visualization of the set of data that is not redundant data. In some embodiments, the data that is not redundant data provides a data set reflecting a soil compaction measurement within the soil area. Some embodiments provide that the soil area is not deeper than 36 inches from a surface of the soil area.

Some embodiments are directed to methods of determining a prescription of tillage in a soil area. Such methods include determining a soil density using at least one ground penetrating radar and at least one electromagnetic interference (EMI) sensor and correlating the soil density using at least one differential geographic positioning system and at least one receiver of the EMI sensor. In some embodiments, the soil compaction degree being above a soil compaction threshold indicates a prescription for tilling the soil area. Some embodiments are directed to methods of determining a prescription of tillage in a soil area. Such methods include determining a soil density using at least one ground penetrating radar and at least one acoustic assemblage and correlating the soil density using at least one differential geographic positioning system and at least one receiver of the at least one acoustic assemblage. The differential geographic positioning system is provided as a non-limiting embodiment for determining location data as some embodiments provide different operations and/or techniques for determining location data. In some embodiments, the soil compaction degree being above a soil compaction threshold indicates a prescription for tilling the soil area.

Some embodiments herein are directed to methods for determining localization of an agricultural vehicle. Such methods include operations of taking a measurement, using at least one sensor, on and beneath a soil surface. In some embodiments, the measurement corresponds to a location in a subsurface soil area. Operations may include receiving, using at least one receiver, the measurement on or beneath the soil surface. The measurement may contain information regarding a physical, chemical and/or biological property corresponding to the location in the subsurface soil area. Operations include transmitting the information regarding the physical, chemical and/or biological property corresponding to the location in the subsurface soil area to a machine configured to use the data from the at least one sensor, and transforming the data into a visual representation of the subsurface soil area. The information is used to localize the agricultural vehicle over a soil area, wherein the location in the subsurface soil area is lower than 18 inches from the surface.

Some embodiments are directed to a processing device that is on a vehicle and that includes a processing circuit and a memory that is coupled to the processing circuit and that includes instructions that, when executed by the processing circuit, causes the processing circuit to perform operations including receiving, from a location device, geographic location data corresponding to a location of the vehicle, receiving, from a sensor that is proximate the vehicle, data relating to a physical, chemical and/or biological characteristic of a soil area, and generating location associated data that relates the geographic location data to the physical, chemical and/or biological characteristic of the soil area at respective locations corresponding to the geographic location data.

Some embodiments are directed to methods that include receiving, using a processing circuit and from a sensor, a data set regarding a physical, chemical and/or biological aspect of a soil area. Operations further include removing, using the processing circuit and from the data set, a redundant data portion, wherein the processing circuit enhances a remaining set of data that is not the redundant data portion. Operations include generating a visualization of the remaining set of data that is not redundant data, wherein the remaining set of data that is not redundant data provides a data set reflecting a soil compaction measurement within the soil area, wherein the soil area is not deeper than 36 inches from a surface of the soil area.

Some embodiments are directed to a tillage vehicle that includes a vehicle that is configured to travel over a soil area, a tilling implement that is configured to implement a tilling prescription plan that identifies tilling depths corresponding to different areas of the soil areas, a location device that is configured to provide geographic location data corresponding to the tillage vehicle, at least one sensor that is caused to move above a surface of the soil area as the vehicle travels thereon and to generate data relating to a physical, chemical and/or biological characteristic of the soil corresponding to the soil area, and a processing circuit that is communicatively coupled to the at least one sensor, to the location device, and to the tillage implement and that is configured to receive the geographic location data and the data relating to the physical, chemical and/or biological characteristic of the soil, and to generate the tilling prescription plan for use by the tilling implement based on the data relating to the physical, chemical and/or biological characteristic of the soil.

Other methods, computer program products, devices and systems according to embodiments of the present disclosure will be or become apparent to one with skill in the art upon review of the following drawings and detailed description. It is intended that all such additional methods, computer program products, and systems be included within this description, be within the scope of the present disclosure, and be protected by the accompanying claims. Moreover, it is intended that all embodiments disclosed herein can be implemented separately or combined in any way and/or combination.

BRIEF DRAWING DESCRIPTION

DETAILED DESCRIPTION

Figure 1:
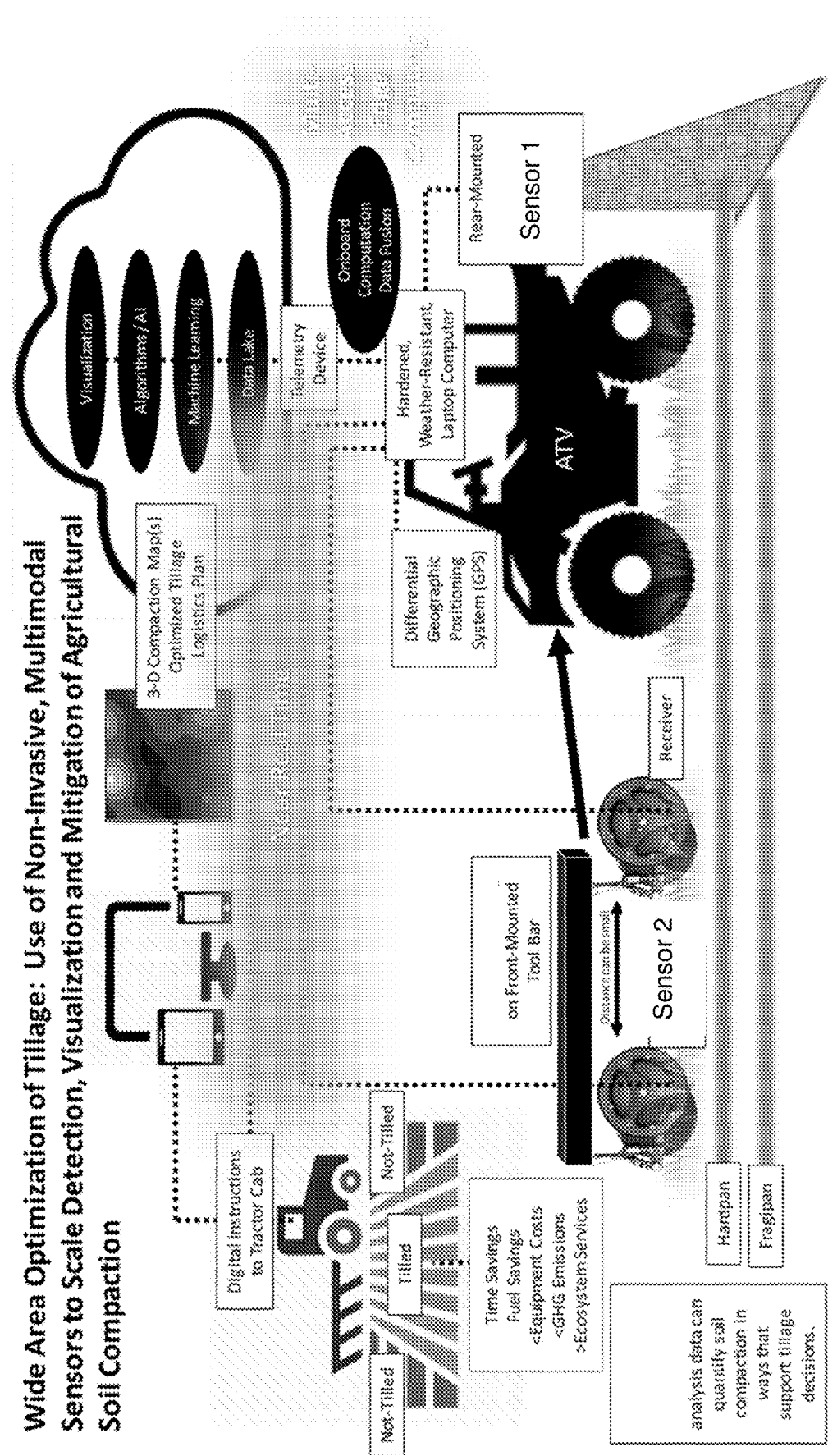
FIG. 1 is a schematic rendering of a system for tillage optimization using non-invasive multimodal sensors according to some embodiments.

In the following detailed description, numerous specific details are set forth in order to provide a thorough understanding of embodiments of the present disclosure. However, it will be understood by those skilled in the art that the present invention may be practiced without these specific details. In other instances, well-known methods, procedures, components and circuits have not been described in detail so as not to obscure the present invention. It is intended that all embodiments disclosed herein can be implemented separately or combined in any way and/or combination.

Some embodiments of the present invention include scalable methods that employ non-invasive, standoff technologies to detect, visualize and quantify intra- and inter-field agricultural soil compaction in near real time. Embodiments may provide economic and environmental advantages to farmers because they provide an initial approach in a novel solution to the worsening problem of root-restricting, subsurface layers of soil created by heavy farm equipment traffic and/or natural soil formation processes. Embodiments herein may enable farmers to confidently forego prophylactic tillage (tillage in the absence of information about soil compaction) and to formulate an optimal tillage plan (deep tillage only when and where it is warranted) for large crop enterprises and acreage.

Some embodiments provide systems including a manually- or autonomously-operated all-terrain vehicle (ATV) that is equipped with a location device, such as a global positioning system (GPS). The vehicle may include a hardened, weather-resistant, laptop computer that directs and receives data from a hardware payload comprising two or more sensors that may be complementary, automated, and/or multimodal. The sensors are selected and integrated specifically for the purpose of optimizing geospatial detection and quantification of soil compaction in three dimensions. The multimodal sensor payload may provide non-invasive hardware designed and operated specifically for the purpose of characterizing agricultural soil compaction.

In some embodiments, the dual sensor payload may include an airborne (above ground), not coupled-to the-ground, ground penetrating radar (GPR). antenna. The GPR antenna may include a horn antenna, a multi-frequency antenna, an array antenna, a phased array antenna and receiver, among others. Embodiments may further include a source of acoustic waves and a corresponding acoustic wave receiver. The acoustic components of embodiments may be deployed at the soil surface inside agricultural double disk openers, inside a small gauge wheel and/or inside a "knife" normally used to apply liquid fertilizers. In such embodiments, tubes intended to deliver fertilizer to the soil surface may be replaced with data transmission cables connecting the invention's laptop to acoustic components of the payload.

In some embodiments, as the payload-bearing ATV moves across the soil surface at 3 to 6 miles per hour, the radar antenna and receiver may be deployed approximately one foot above the soil surface and the acoustic or seismic components may be deployed at the soil surface. Data from the radar and acoustic sensors are collected and transmitted directly to the hardened laptop. Some embodiments provide that the data are, via automated algorithms and analytics unique to such embodiments, transformed, fused and combined with GPS coordinates and elevation data such that the location and depth of agricultural soil compaction may be defined. In some embodiments, field by field, the magnitude of the soil compaction problem may be diagnosed across a crop production enterprise. Pursuant to these calculations performed by the onboard laptop computer, embodiments may further include a telemetry device connected to the laptop computer. In some embodiments, the telemetry device may transmit the transformed and fused data directly to a multiaccess "edge" cloud computing environment where the data may be deposited into a data lake structure. Some embodiments provide that, in the cloud computing environment, additional algorithms, analytics and machine learning protocols may access and utilize data from the data lake structure to create a visual image of subsurface soil compaction.

The visual image may depict the portions of a geographical area, i.e. a field or landscape, that are compacted, where, in that geographical area, soil compaction exists that would restrict root growth and the depth of root-restricting compaction. Fusion of elevation data, i.e. a digital elevation model, into this visualization of soil compaction is also performed to provide additional richness to the data. For a farmer, land manager or agronomist, inclusion of elevation data in the data fusion-visualization process puts subsurface soil compaction into context relative to slope, soil type, cultivar performance, fertilizer use efficiency and/or water use efficiency.

Use of the onboard laptop to perform the calculative workload and immediate movement of that mathematical work product into the aforementioned multi-access cloud computing environment via the onboard telemetry device gives the present embodiments extremely low latency. Additional calculations may be performed and data transformation may occur in the cloud computing environment. In this manner, a farmer or interested party can, via an internet interface and mobile telephone, tablet and/or computer, view soil compaction within a field, among fields in a farming unit, across a landscape or throughout an entire crop production enterprise. Given the computational design and telemetry integrated into the present embodiments, agricultural soil compaction may be characterized in real to near real time.

Reference is now made to FIG. 1, which is a schematic rendering of a system for tillage optimization using non-invasive multimodal sensors according to some embodiments. As illustrated, a vehicle, such as an all-terrain vehicle (ATV) may have a first sensor (Sensor 1) that is mounted to the rear thereof. Sensor 1 may include any number of sensor technologies including but not limited to GPR, seismic, acoustic, laser and/or electromagnetic induction sensor technologies. In some embodiments, a second sensor (Sensor 2) may be mounted to the front of the vehicle and may include any number of sensor technologies, including but not limited to GPR, seismic, acoustic, laser and/or electromagnetic induction sensor technologies. Some embodiments provide the Sensor 1 and Sensor 2 include sensor technologies that are different from one another.

In some embodiments, a computing device may be supported by the vehicle and may receive and/or store sensor data that is received from Sensors 1 and 2. Some embodiments provide that the computer comprises a hardened weather-resistant laptop computer, but such embodiments are non-limiting as the computer may include a different form factor including mobile telephone, tablet, and/or fixedly mounted computer.

A location and/or navigation device may be provided in the vehicle and may generate geographic location information corresponding to the vehicle. For example, some embodiments provide that the location and/or navigation device comprises a differential geographic positioning system (GPS). Location data from the location and/or navigation device may be provided to the computer. In some embodiments, the computer may associate the location data with the sensor data that is received from Sensor 1 and/or Sensor 2. In this manner, the soil compaction data corresponding to each location that is traversed by the vehicle may be determined to provide location specific soil compaction data.

A telemetry device may transmit the location specific soil compaction data from the computer to a remote computer and/or data repository using any combination of wired and/or wireless communication protocols and/or technologies. In some embodiments, the remote computer may perform additional analysis and may generated a three-dimensional compaction map corresponding to the location specific soil compaction data among others.

In some embodiments, a tillage prescription plan that includes data identifying which areas of the soil should be tilled. The tillage prescription plan may further include data regarding how deep different areas should be tilled to overcome the soil compaction. In some embodiments, the tillage prescription plan may be transmitted to one or more agriculture vehicles that include automated tilling implements that are towed and/or mounted thereto. For example, digital instructions may be transmitted to a tractor cab to control the tilling implement to till the soil surface according to the tillage prescription plan.

By selectively tilling different portions of the soil surface, advantages may include time savings, fuel savings, equipment cost savings, green-house gas emission reductions, and ecological system damage reduction.

Figure 2:
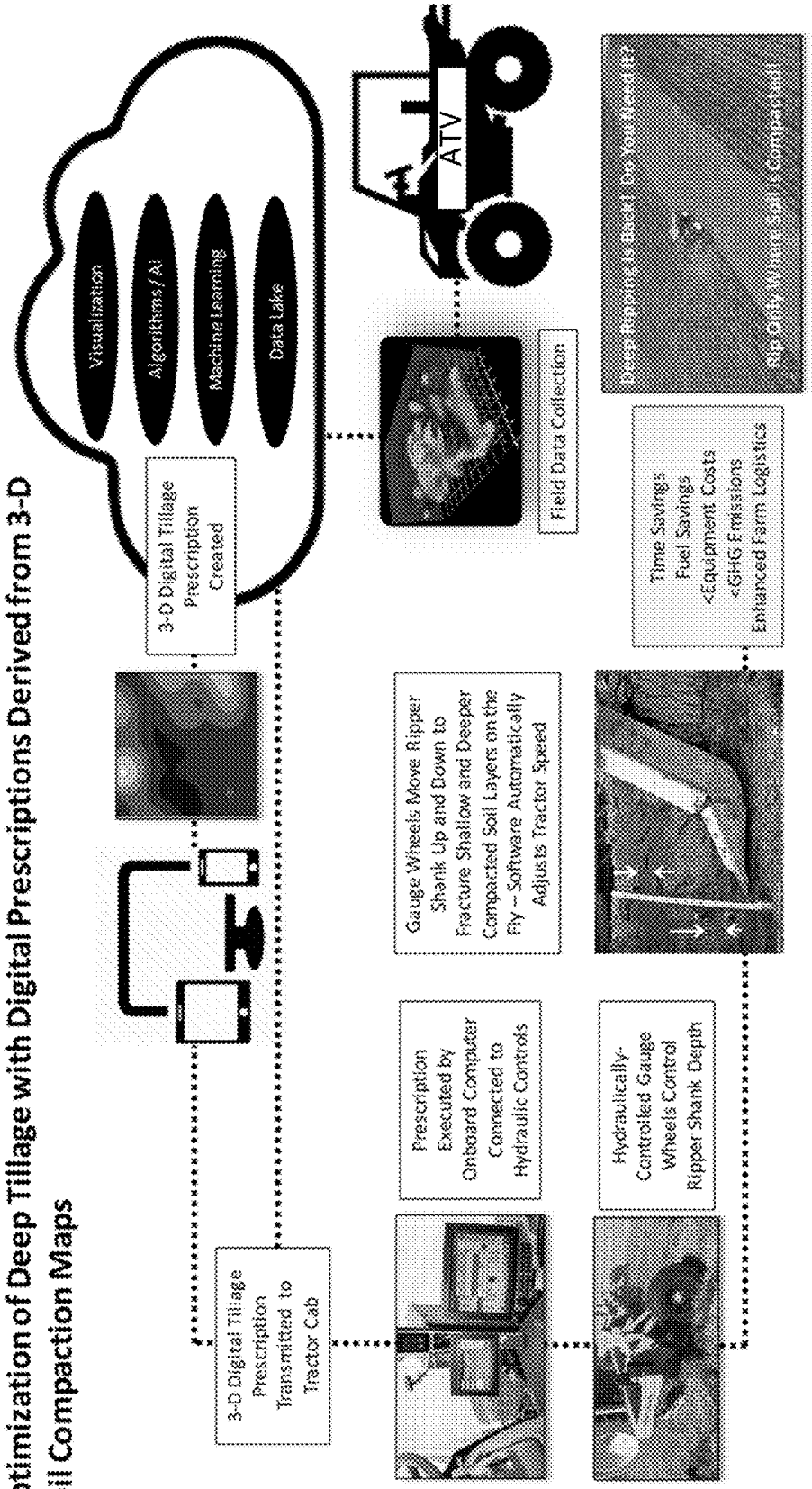
FIG. 2 is a schematic rendering of a system for tillage optimization using digital prescriptions derived from three-dimensional maps according to some embodiments.

Reference is now made to FIG. 2, which is a schematic rendering of a system for tillage optimization using digital prescriptions derived from three-dimensional maps according to some embodiments. As illustrated, a vehicle, such as an all-terrain vehicle (ATV) described in reference to FIG. 1 is provided. Field data collection is generated and a three-dimensional tillage prescription is generated. The three-dimensional tillage prescription plan is transmitted to the cab of a tractor or other agriculture equipment and the tillage prescription plan is executed by an on-board computer that is connected to hydraulic controls. Hydraulically controlled gauge wheels may control a ripper shank depth. The gauge wheels may move the ripper up and down to fracture shallow and deeper compacted layers in real time with the software automatically adjusting the tractor speed to during the operation.

Figure 3:
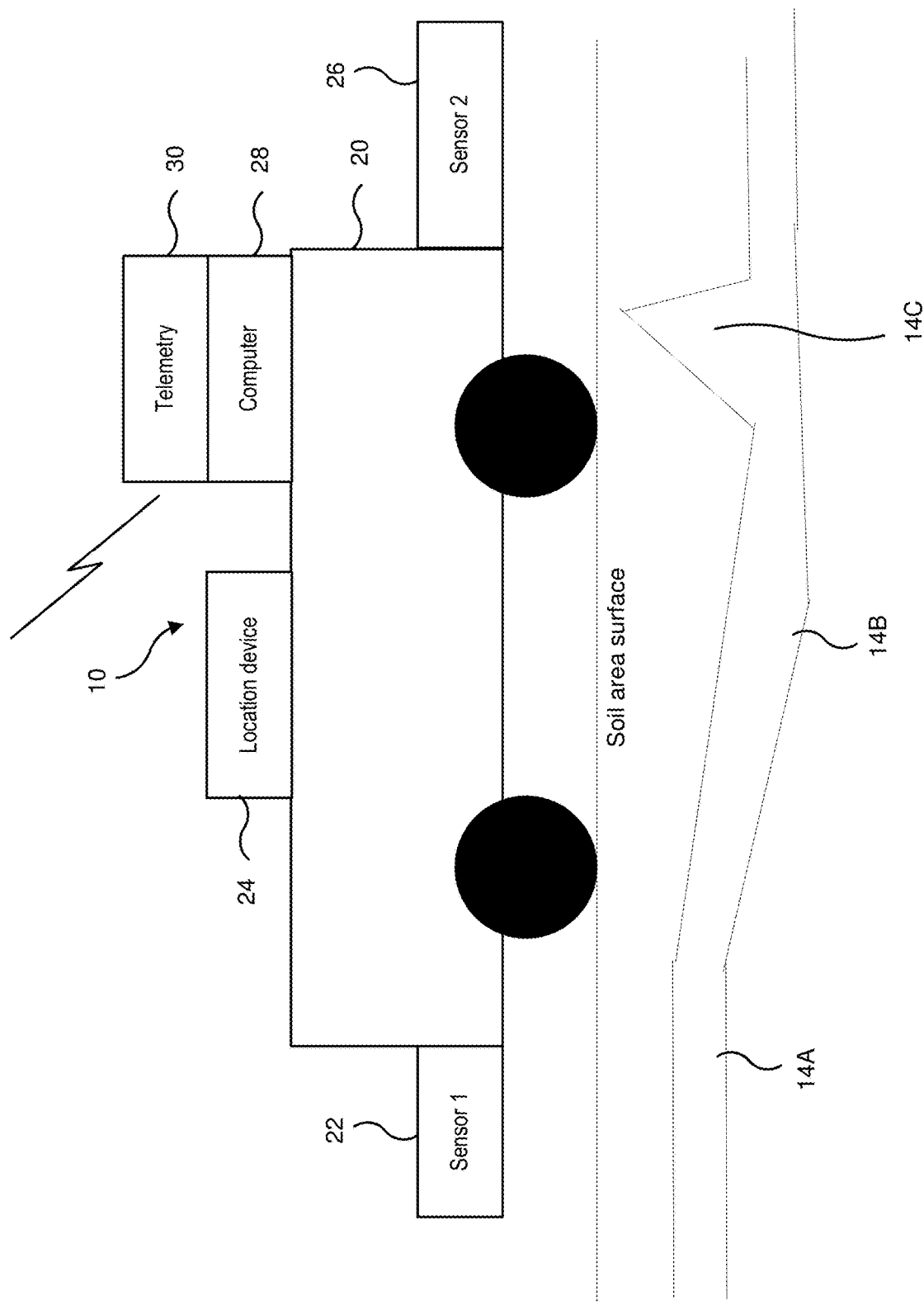
FIG. 3 is a schematic block diagram illustrating a system for tillage optimization using non-invasive multimodal sensors according to some embodiments.

Reference is now made to FIG. 3, which is a schematic block diagram illustrating a system for tillage optimization using non-invasive multimodal sensors according to some embodiments. A system 10 according to some embodiments includes a vehicle 20 that is configured to travel over a soil area. A location device 24 is configured to provide geographic location data corresponding to the vehicle 20. At least one sensor 22, 26 is mounted to the vehicle to cause the at least one sensor to move above a surface of the soil area as the vehicle travels thereon and to generate data relating to a physical, chemical and/or biological characteristic of the soil corresponding to the soil area. Depending on the sensor technology, the at least one sensor 22 (Sensor 1) may include a non ground-coupled sensor. A computer 28 is communicatively coupled to the at least one sensor 22, 26 and to the location device 24. The computer may be configured to receive the geographic location data and the data relating to the physical, chemical and/or biological characteristic of the soil. The computer 28 may be further configured to generate location associated data relating to the physical, chemical and/or biological characteristic of the soil corresponding to the soil area.

In some embodiments, the data relating to the physical, chemical and/or biological characteristic of the soil correlates to soil bulk density. In some embodiments, soil bulk density may be expressed as soil compaction data. Some embodiments provide that the data relating to the physical, chemical and/or biological characteristic of the soil includes soil moisture.

Some embodiments provide that the soil area includes multiple soil area elements. For example, a soil element may correspond to a specific area, size and/or shape of the soil surface. In some embodiments, each soil area element corresponds to a specific geographic location and a corresponding location associated soil compaction data value. Some embodiments provide that each soil area element includes an area that is in a range from about one square foot to about ten acres. Such embodiments are non-limiting examples, however, as a soil element may be larger than ten acres.

In some embodiments, a sensor 22, 26 comprises a ground penetrating radar (GPR). Some embodiments provide that the GPR is configured to operate in a frequency range of about 10 MHz to about 5 GHz. Such embodiments are non-limiting examples, however, as the operational frequency range may be less than 10 MHz or greater than 5 GHz. In some embodiments, the GPR is configured to operate in a frequency range of about 100 MHz to about 600 MHz. In some embodiments, the GPR is configured to operate in a frequency range of about 200 MHz to about 800 MHz. In some embodiments, the GPR is configured to operate at or above about 100 MHz. In some embodiments, the GPR is configured to operate at or below about 800 MHz. Some embodiments provide that the GPR is configured to operate in VHF, UHF and/or L-Band frequency ranges. In some embodiments, the GPR is a non ground-coupled antenna. Some embodiments provide that the non ground-coupled antenna includes a horn antenna and/or an array antenna.

In some embodiments, the GPR is configured to operate in a plurality of different frequency ranges. Some embodiments provide that the GPR is configured to simultaneously operate in different frequency ranges.

In some embodiments, at least one sensor 22, 26 is a non-invasive sensor relative to the surface of the soil area. Some embodiments provide that at least one sensor 22, 26 is configured to move in a range from at the surface of the soil area to about six feet above the surface of the soil area. However, such range is non-limiting as the sensor 22, 26 may be configured to operate at an elevation that is higher than six feet relative to the soil surface.

Some embodiments include a sensor support that is configured to physically support at least one sensor 22, 26 and to be pulled across the surface of the soil area by the vehicle 20. In some embodiments, the sensor support is and/or includes a self-propelled vehicle that is separate from the vehicle or towed vehicle that is coupled to the vehicle. Some embodiments provide that the location associated soil compaction data includes elevation data corresponding to the soil compaction.

In some embodiments, the vehicle comprises a self-driving vehicle and is configured to traverse the soil area in a path that is defined by a coverage plan that is based on the geographic location data. For example, a terrestrially operating vehicle such as a self-driving ATV, cart, or tractor may use the location data in conjunction with a coverage plan to traverse the soil are in the predefined path.

Figure 4:
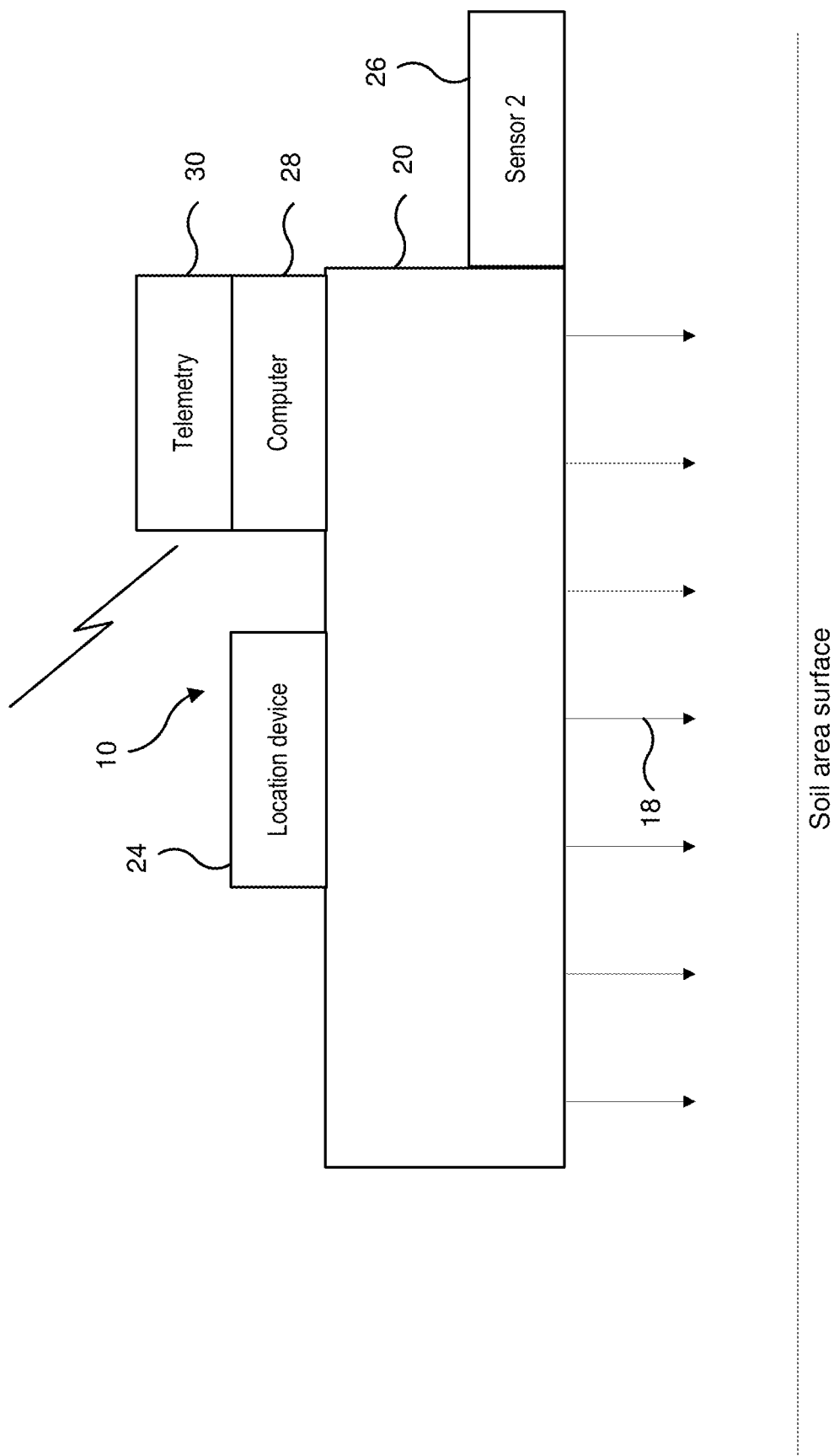
FIG. 4 is a schematic block diagram illustrating a system as described in FIG. 3 including an airborne vehicle according to some embodiments.

Brief reference is now made to FIG. 4, which is a schematic block diagram illustrating a system as described in FIG. 3 including an airborne vehicle according to some embodiments. In some embodiments, the vehicle comprises an airborne vehicle and is configured to fly over the soil area based on self-generated lift 18. In some embodiments, the airborne vehicle is an autonomously flying drone that operates according to a predefined coverage plan that may define elevation, speed and path. Some embodiments provide that the drone is tethered to a ground station and/or another vehicle while other embodiments provide that the drone is untethered. In some embodiments, the drone may include telemetry 30 for transmitting the generated data during and/or after flight. Some embodiments provide that the drone include on board memory for storing the generated data.

In some embodiments, the airborne vehicle is configured to fly over the soil area in a pattern that is defined by a coverage plan that is based on the geographic location data. Although the airborne vehicle is illustrated as including only a second sensor 26, embodiments herein provide that more than one sensor may be mounted thereto.

Referring back to FIG. 3, some embodiments provide that the computer 28 is further configured to generate a tillage prescription plan for the soil area that is based on the location associated soil compaction data. In some embodiments, the tillage prescription plan includes data that identifies a first portion of soil area not to till and a second portion of the soil area to till. Some embodiments provide that the tillage prescription plan includes data that identifies multiple different portions of the soil surface that each correspond to a different tilling depth. In some embodiments, the tillage prescription plan includes three-dimensional tillage data that defines a location corresponding to a portion of the soil area and a tilling depth that corresponds to the location. In some embodiments, at least one sensor 22, 26 is a non-invasive sensor and the three-dimensional tillage data is graphically represented based on data generated using the non-invasive sensor.

Some embodiments provide that the computer 28 is coupled to telemetry 30 for transmitting tillage prescription data to a tilling vehicle that includes a tilling implement. Although not illustrated, embodiments herein contemplate that various intervening devices and/or equipment may be in a communication path between the computer 28 and a tilling implement. The tilling vehicle and/or the tilling implement are configured to implement the tillage prescription plan by varying tillage depth based on a tilling location.

In some embodiments, the tilling implement is propelled by the tilling vehicle. Some embodiments provide that the tilling implement varies the tilling depth based on using an electrical, mechanical and/or hydraulic positioning component to vary the depth of the tilling implement and thus the tilling depth. Some embodiments provide that the tilling implement is mounted to the tilling vehicle and is positioned to vary the tilling depth. In some embodiments, the tillage prescription plan is implemented automatically by the tilling vehicle and/or the tilling implement.

Some embodiments provide that at least one of the sensors 22, 26 is located on a front of the vehicle 20 and is configured to generate the data corresponding to the soil area in the front of the vehicle 20. In such embodiments, the vehicle 20 may include a tilling implement that is at a rear portion of the vehicle 20 and that is configured to vary the tilling depth of the soil area behind the vehicle 20. In some embodiments, the tillage prescription data is transmitted to tilling vehicle in substantially real-time relative to generation of the location associated soil compaction data.

Some embodiments provide that the computer 28 is located at the vehicle and that a second computer is remote from the vehicle 20. The computer 28 may be further configured to generate the location associated soil compaction data and to transmit the location associated compaction data to a data repository that is accessible by the second computer. In some embodiments, the second computer is configured to receive the location associated soil compaction data and to generate a tillage prescription plan for the soil area that is based on the location associated soil compaction data. In some embodiments, the second computer is further configured to transmit the tillage prescription plan to a tilling vehicle.

In some embodiments, the computer 28 is further configured to generate the location associated physical, chemical and/or biological characteristic data of the soil and to generate a tillage prescription plan for the soil area that is based on the location associated physical, chemical and/or biological characteristic data. For example, FIG. 3 includes a cross-sectional view of compacted soil portions 14. The compacted soil portions include a first compacted soil portion 14A that is at a first depth below the soil surface and a second compacted soil portion that is at a second depth below the soil surface. Additionally, a subsurface feature 14C may be used to provide and/or confirm location data based on mapping out such compaction features. In some embodiments, the vehicle 20 includes a tilling implement and the computer is configured to perform the tillage prescription plan using the tilling implement on the vehicle 28.

Some embodiments provide that at least one sensor includes a first sensor 22 that includes a first sensor technology and a second sensor 26 that includes a second sensor technology that is different from the first sensor technology. In some embodiments, the first sensor 22 is mounted to a front of the vehicle 20 and the second sensor 26 is mounted to the rear of the vehicle 20. In some embodiments, the first sensor technology is one of GPR, seismic, acoustic, laser and electromagnetic induction technologies and the second sensor technology is a different one of GPR, seismic, acoustic, laser and/or electromagnetic induction technologies. In some embodiments, the soil compaction data from the first sensor 22 and the soil compaction data from the second sensor 26 are used to generate composite location associated soil compaction data. Some embodiments provide that the computer 28 is further configured to generate location data corresponding to the vehicle 20 based on the location associated soil compaction data. In some embodiments, the first and/or second sensor may include a stand-off sensor. As provided herein, a stand-off sensor may include a sensor that may use electromagnetic, optical, seismic and/or acoustical methods to measure the properties of soil without actually physically contacting the soil surface. In some embodiments, measurements received using a stand-off sensor may be referred to as remote sensing.

Some embodiments provide that a stand-off sensor may traverse the top surface of the soil without substantially penetrating and/or otherwise disturbing the soil. Whereas soil resistance, soil density and soil compaction, i.e. hard soil that resists root penetration and water movement, may generally be estimated via invasive methods that may include penetrometers, probes and/or shovels, embodiments herein may employ active sensors, in contrast to passive sensors, that generate data that, in turn, may be combined or fused to provide an estimate of soil resistance, density and/or compaction. That estimate may be derived in substantially real time without penetrating the soil surface. In this manner, sensors according to some embodiments may be non-invasive and may be referred to as "standoff" sensors.

In some embodiments, the data relating to the physical, chemical and/or biological characteristic of the soil includes a correlation with a soil aggregate stability value. As used herein, the term "soil aggregate stability" refers to a quantitative soil health parameter that refers to the ability of soil to bind together in "aggregates" that provide pore space and that may resist the influence of outside forces, e.g. driving rain, heavy axle loads and/or excessive tillage, among others. Good soil aggregate stability suggests that a soil is not overly dense or compacted. In some embodiments, the data relating to the physical, chemical and/or biological characteristic of the soil includes a correlation with an organic matter content value. The organic matter content value may refer to the amount of organic content is determined to be in the soil at a given location. In some embodiments, the data relating to the physical, chemical and/or biological characteristic of the soil includes a correlation with a soil tilth value.

Soil tilth is an expression that describes the ability of plowed soils to support crop growth. For example, with GPR and EMI, we may be able to electromagnetically describe and quantify soil tilth and thereby provide in-field soil health assessments. The ability to describe and quantify soil tilth using, for example, GPR and EMI, may eliminate and/or reduce the need to perform other, more disruptive measurements to determine soil density. Soil bulk density (gm/cm3 volume of a soil sample), soil aggregate stability (weight of sieved aggregates/total dry or wet weight of a soil sample) and soil tilth (combined stability of aggregated soil particles, moisture content and degree of aeration) may all uniquely describe the physical condition of soil and the site-specific ability of a soil to support crop production. All three parameters may manifest soil compaction, if present. Some embodiments provide that all three parameters can be highly correlated with standoff sensor measurements, e.g. GPR and EMI and/or multimodal GPR/EMI, to make valid inferences about soil heath that can be improved via machine learning. Soil aggregate stability and soil tilth, in particular, lend themselves to novel estimation via standoff multimodal sensors paired with machine learning. Some embodiments provide that the soil tilth value may be determined based on the soil aggregate stability. Some embodiments provide that the soil tilth value may be determined based on a soil compaction data value.

Figure 5:
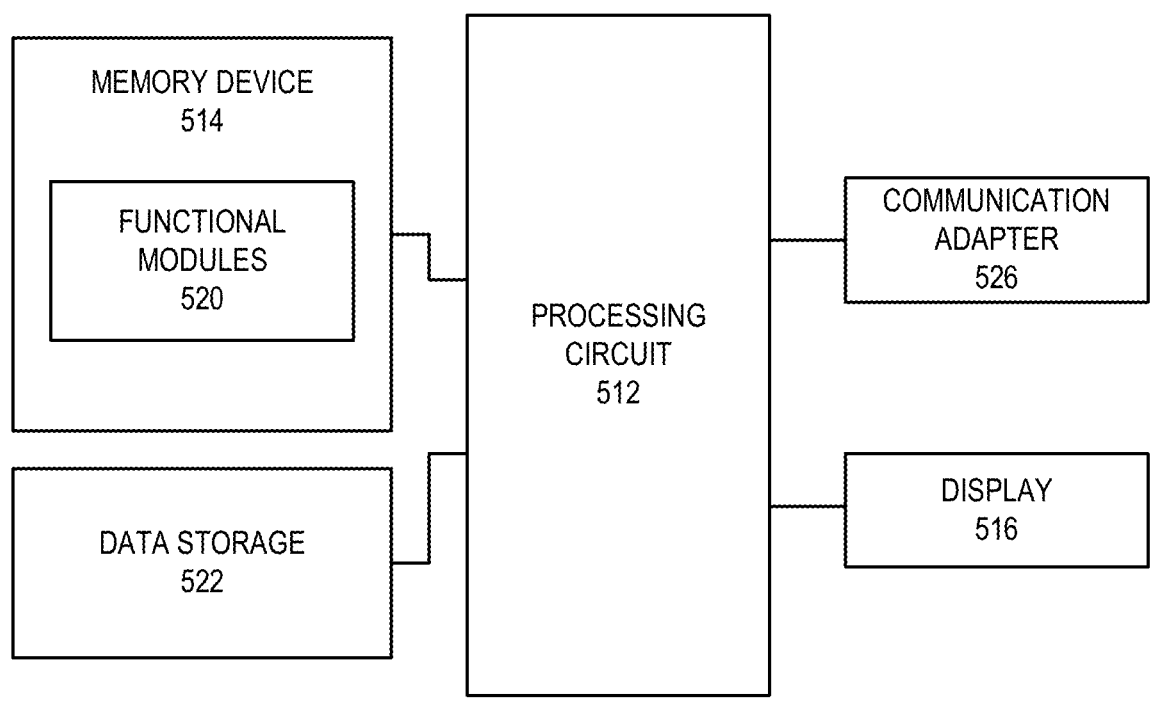
FIG. 5 is a schematic block diagram illustrating an electronic configuration for a computer according to some embodiments.

FIG. 5 is a schematic block diagram illustrating an electronic configuration for a computer according to some embodiments. As shown in FIG. 5, the computer 28 may include a processing circuit 512 that controls operations of the computer 28. Although illustrated as a single processing circuit, multiple special purpose and/or general-purpose processors and/or processor cores may be provided in the computer 28. For example, the computer 28 may include one or more of a video processor, a signal processor, a sound processor and/or a communication controller that performs one or more control functions within the computer 28. The processing circuit 512 may be variously referred to as a "controller," "microcontroller," "microprocessor" or simply a "computer." The processor may further include one or more application-specific integrated circuits (ASICs).

Various components of the computer 28 are illustrated as being connected to the processing circuit 512. It will be appreciated that the components may be connected to the processing circuit 512 through a system bus, a communication bus and controller, such as a USB controller and USB bus, a network interface, or any other suitable type of connection.

The computer 28 further includes a memory device 514 that stores one or more functional modules 520.

The memory device 514 may store program code and instructions, executable by the processing circuit 512, to control the computer 28. The memory device 514 may also store other data such as image data, event data, user input data, and/or algorithms, among others. The memory device 514 may include random access memory (RAM), which can include non-volatile RAM (NVRAM), magnetic RAM (ARAM), ferroelectric RAM (FeRAM) and other forms as commonly understood in the gaming industry. In some embodiments, the memory device 514 may include read only memory (ROM). In some embodiments, the memory device 514 may include flash memory and/or EEPROM (electrically erasable programmable read only memory). Any other suitable magnetic, optical and/or semiconductor memory may operate in conjunction with the gaming device disclosed herein.

The computer 28 may further include a data storage device 522, such as a hard disk drive or flash memory. The data storage device 522 may store program data, player data, audit trail data or any other type of data. The data storage device 522 may include a detachable or removable memory device, including, but not limited to, a suitable cartridge, disk, CD ROM, DVD or USB memory device.

Figure 6:
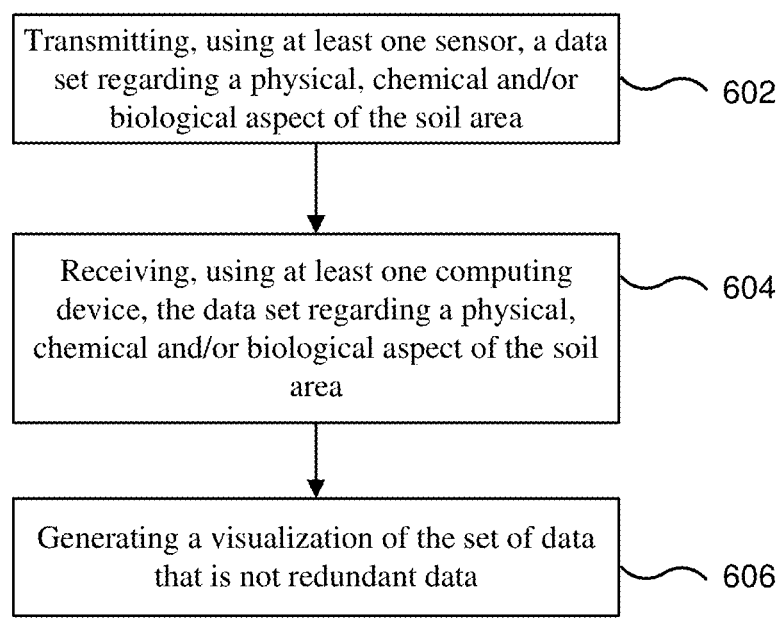
FIG. 6 is a flowchart of operations according to some embodiments herein.

Reference is now made to FIG. 6, which is a flowchart of operations according to some embodiments herein. Operations include transmitting, using at least one sensor, a data set regarding a physical aspect of a soil area (block 602). In some embodiments, the sensor is a ground penetrating radar. Some embodiments provide that the at least one sensor includes a ground penetrating radar and an electromagnetic induction device. Some embodiments provide that the at least one sensor is a ground penetrating radar and a seismic transmission device.

Operations may include receiving, using at least one computing device, the data set regarding a physical aspect of the soil area (block 604). Some embodiments provide that the computing device removes a set of redundant data and enhances a set of data that is not redundant data. Operations may further include generating a visualization of the set of data that is not redundant data (block 606). In some embodiments, the data that is not redundant data provides a data set that reflects a soil compaction measurement within the soil area. Some embodiments provide that the soil area is not deeper than 36 inches from a surface of the soil area. In some embodiments, the visualization of the set of data determines a tillage program. Some embodiments provide that the measurement of soil compaction is used to determine a soil tillage prescription.

Figure 7:
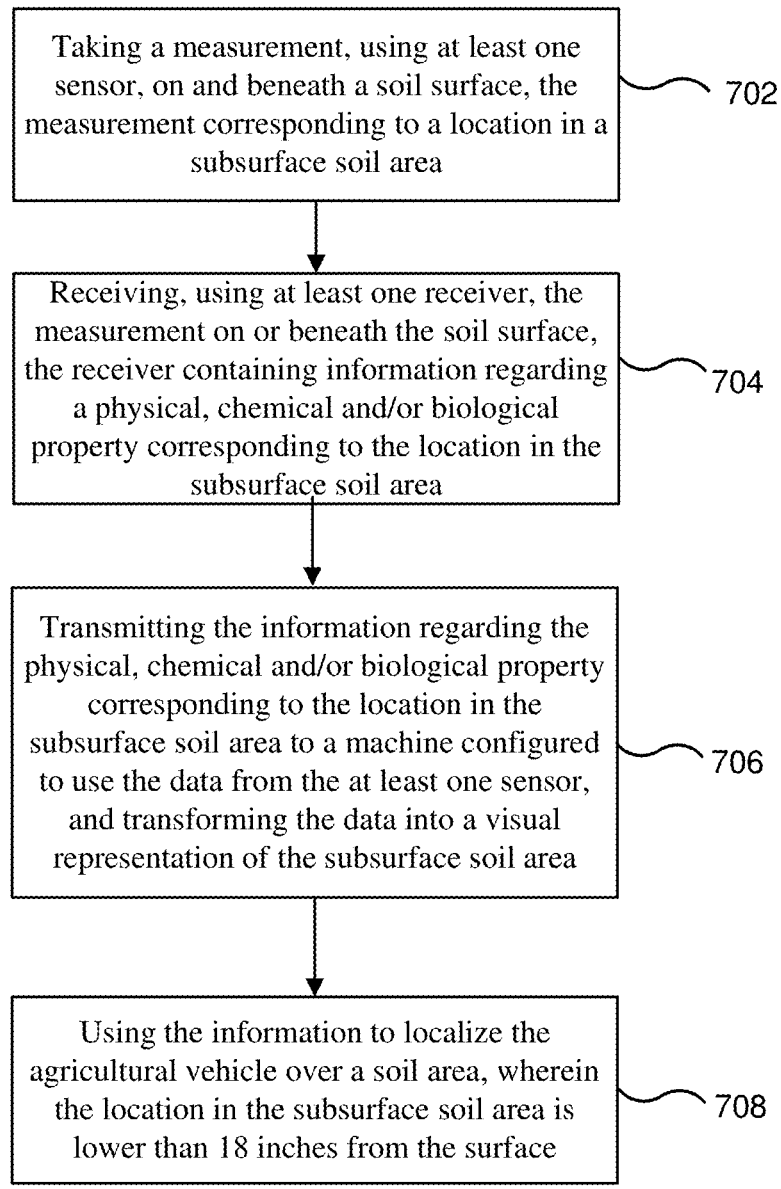
FIG. 7 is a flowchart of operations according to some embodiments herein.

Reference is now made to FIG. 7, which is a flowchart of operations according to some embodiments herein. Operations include taking a measurement, using at least one sensor, on and beneath a soil surface, the measurement corresponding to a location in a subsurface soil area (block 702). Operations further include receiving, using at least one receiver, the measurement on or beneath the soil surface, the receiver containing information regarding a physical, chemical and/or biological property corresponding to the location in the subsurface soil area (block 704). Operations include transmitting the information regarding the physical, chemical and/or biological property corresponding to the location in the subsurface soil area to a machine configured to use the data from the at least one sensor and transforming the data into a visual representation of the subsurface soil area (block 706). Further the information may be used to localize the agricultural vehicle over a soil area, wherein the location in the subsurface soil area is lower than 18 inches from the surface (block 708).

Figure 8:
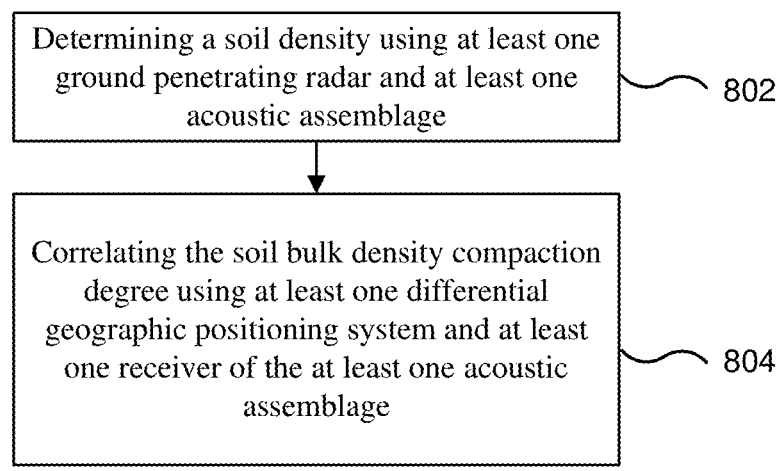
FIG. 8 is a flowchart of operations according to some embodiments herein.

Reference is now made to FIG. 8, which is a flowchart of operations according to some embodiments herein. Operations include determining a soil density using at least one ground penetrating radar and at least one acoustic assemblage (block 802). Operations further include correlating the soil bulk density compaction degree using at least one differential geographic positioning system and at least one receiver of the at least one acoustic assemblage (block 804). In some embodiments, a soil compaction threshold may be determined and, responsive to a soil area having the soil compaction degree that exceeds the soil compaction threshold, a prescription for tilling that soil area may be generated.

Some embodiments provide that the soil compaction threshold is determined through the removal of a redundant data set of a physical aspect of the soil area and is determined by a soil compaction measurement of about 0 PSI to about 1000 PSI. In some embodiments, the soil compaction threshold is determined a soil compaction measurement of about 100 PSI to about 400 PSI. In some embodiments, the soil compaction threshold is determined a soil compaction measurement of about 150 PSI to about 300 PSI.

Some embodiments provide that the soil compaction threshold may be determined by a soil compaction measurement of about 0 g/cm$^3$ to about 2.5 g/cm$^3$. Some embodiments provide that the soil compaction threshold may be determined by a soil compaction measurement of about 1.0 g/cm$^3$ to about 2.0 g/cm$^3$. Some embodiments provide that the soil compaction threshold may be determined by a soil compaction measurement of about 1.2 g/cm$^3$ to about 1.8 g/cm$^3$. In some embodiments, the soil compaction threshold may correlate to a soil density value. According to embodiments herein, such ranges are non-limiting as other compaction ranges are contemplated herein. As used herein, PSI may refer to soil resistance and may also relate to compaction. Actual compaction thresholds must be determined experimentally for different crops in different soil types based on field trial results. The compaction thresholds may be a qualitative threshold that may be determined by physical inspection including by digging an inspection hole, among others In some embodiments, the data set regarding a physical aspect of the soil is analyzed with a neural network. A neural network according to some embodiments includes a training set that includes a data set regarding the soil area. The data set may include weather, physical, chemical, structural, topographical, and/or geographical data. In some embodiments, a visualization of the data set may depict the bulk density of the soil area and may be displayed in at least two dimensions. For example, some embodiments provide that the visualization may be displayed in three or more dimensions. Some embodiments provide that a prescription for tilling the soil area based on the visualization of the data set. In some embodiments, the at least two dimensions include depth and density of the soil area and the visualization includes at least one other dimension.

Although discussed herein as including neural networks for processing and/or analyzing data, some embodiments herein may rely on one or more algorithms including statistical and/or machine learning techniques. Such labelling techniques may include, but are not limited to labeling of data with semi-supervised classification, labeling of data with unsupervised classification, DBSCAN, and/or K-means clustering, among others. Such classification techniques may include, but are not limited to linear models, ordinary least squares regression (OLSR), stepwise regression, multivariate adaptive regression splines (MARS), locally estimated scatterplot smoothing (LOESS), ridge regression, least absolute shrinkage and selection operator (LASSO), elastic net, least-angle regression (LARS), logistic regression, decision tree, other tree-based algorithms (e.g. ADA-Boost), support vector machine, and neural network based learning. Neural network-based learning may include feed forward neural networks, convolutional neural nets, recurrent neural nets, long/short term memory neural, auto encoders, generative adversarial networks [especially for synthetic data creation], radial basis function network, and any of these can be referred to as "deep" neural networks. Additionally, ensembling techniques to combine multiple models, bootstrap aggregating (bagging), random forest, gradient boosted models, and/or stacknet may be used.

Additionally, in some embodiments, training data may optionally be transformed using dimension reducing techniques, such as principal components analysis, among others.

Laser-induced breakdown spectroscopy. To accelerate collection and measurement of soil nutrient levels, some embodiments use LIBS, a standoff, laser-based technology that has, to date, been used, for the most part, to detect metallic elements in civil engineering and industrial applications. Some embodiments include portable LIBS units. Laser-induced breakdown spectroscopy has been adapted for use in aqueous environments and, in the laboratory, it has been used to measure elements in soil. Some embodiments provide that LIBS can measure elements that are essential to a crop plant as well as elements customarily found on a soil test report. In addition, LIBS has been used to estimate soil carbon, a viable surrogate for OM values found on soil test reports. In some embodiments, LIES may be used to measure soil nutrients, in situ, in a farm field. Some embodiments provide that automated LIBS are used, in either multimodal or autonomous fashion, for agricultural purposes.

Ground-Penetrating Radar. Ground-penetrating radar may be used to detect the presence of soil roots for plant phenotyping purposes. In some embodiments, GPR is used to diagnose and mitigate the increasing soil compaction problem that plagues crop producers and dramatically reduces crop productivity.

Electromagnetic Induction. Electrical conductivity measurements obtained with an EMI sensor may be used to designate management zones within fields, i.e. intra-field areas that are contiguous and similar enough in texture and water holding capacity to be managed as a single entity.

Some embodiments provide a mobile, self-propelled, soil health and management laboratory (MSHML). It can be operated autonomously or manually. A multimodal trifecta of sensors may be deployed in combination. The MSHML payload comprises simultaneous use of ground-penetrating radar (GPR), laser-induced breakdown spectroscopy (LIBS) and electromagnetic induction (EMI) sensors, deployed, in this case, to collect and fuse information about physical, chemical and biological characteristics of soil. Embodiments provide a data upload capability and communications link that connects the MSHML to a cloud computing environment.

In some embodiments, placement of these particular sensors, GPR, EMI and LIBS, onto an autonomous, all-terrain vehicle (ATV), and integration of those sensors with other digital technologies, on and off the ATV constitute an automated, standoff method for assessing soil health and quality. Via the machine and methods presented herein, one can collect, transmit and display reliable information about physical, chemical and biological characteristics of soil in near real time, in effect, delivering essential information a farmer needs to manage for a healthy soil. Some embodiments provide a near real time assessment of soil health, delivered in a context suitable for crop producer use. In some embodiments, the MSHML is a self-propelled suite of devices, sensors and technologies used in combination for the purpose of monitoring soil health. The machine consists of an ATV that can be operated manually or autonomously. The ATV may transport an automated, multimodal payload consisting of GPR, LIBS and EMI sensors. Other components on the ATV are integrated with the stacked sensor payload. Components include a power source, an electrical converter, a computer hardened for outdoor use, a differential global positioning system (GPS), a conventional or multispectral camera and a wireless data communication system. Collectively, the "stacked" sensor payload and these elements provide near real time wireless transmission of data describing physical, chemical and biological characteristics of soil into a cloud computing enterprise.

Some embodiments use commercial technology to wirelessly transmit data directly into a computing environment architecture, such as a hybrid enterprise cloud, the enterprise being a data lake, i.e. a database configuration that: manages structured and unstructured data, supports visual analytics and facilitates machine learning focused upon below ground attributes of soil. Therein, computer code, algorithms and analytics fuse data from the respective sensors to generate unique visualizations and assessments relevant to soil health and management.

In some embodiments, in a directed sampling mode, responding to wireless commands from its laptop control station, the machine moves to the desired latitude and longitude in a farm field. In some embodiments, the MSHML uses a nearest neighbor, statistical algorithm that considers historical productivity, elevation and other parameters to select optimum sampling sites. Finally, the MSHML can be programmed to grid sample, i.e. to collect measurements at coordinates corresponding to a grid, e.g. the 2.5-acre to 5.0-acre grid that is commonly used for variable rate fertilizer application.

In some embodiments, the GPR sensor is mounted beneath the ATV and connected to the onboard computer that receives its instructions from a laptop control station. Upon reaching the proper coordinates in either directed or grid sampling mode, the automated MSHML collects soil compaction data using its GPR sensor, operating at, for example, 500 MHZ.

As part of its mission to assess soil health, embodiments herein represent automated use of GPR to measure soil compaction across extensive acreage, create the first, 3-dimensional, intra-field map of soil compaction that is translated into the first 3-dimensional, digital "prescription" that can "filled" by a deep tillage implement capable of responding to such a prescription and transform GPR measurements into a compaction mitigation plan for crop producers.

In some embodiments, a processing device, such as the computer 28 referenced in FIGS. 3-5, may be removable and/or fixably mounted to and/or supported by a vehicle 20. In some embodiments, the processing circuit 512 may be configured to receive, from a location device, geographic location data corresponding to a location of the vehicle. The processing circuit 512 may be further configured to receive, from a sensor that is proximate the vehicle, data relating to a physical, chemical and/or biological characteristic of a soil area. The processing circuit 512 may further generate location associated data that relates the geographic location data to the physical, chemical and/or biological characteristic of the soil area at respective locations corresponding to the geographic location data.

Some embodiments provide that the sensor is caused to move above a surface of the soil area as the vehicle travels thereon and to generate the physical, chemical and/or biological characteristic data corresponding to the soil area. In some embodiments, the data relating to the physical, chemical and/or biological characteristic of the soil includes electrical conductivity.

In some embodiments, the soil area includes multiple soil area elements that may each correspond to a specific geographic location and a corresponding location associated soil compaction data value. Some embodiments provide that each soil area element includes an area that is in a range from about one square foot to about ten acres.

In some embodiments, the first and/or second sensor 22, 26 includes a ground penetrating radar (GPR) that may be configured to operate in a frequency range of about 10 MHz to about 5 GHz. In some embodiments, the GPR is configured to operate in a frequency range of about 200 MHz to about 800 MHz. In some embodiments, the GPR is configured to operate at or above about 100 MHz. In some embodiments, the GPR is configured to operate at or below about 800 MHz. Some embodiments provide that the GPR is configured to operate in VHF, UHF and/or L-Band frequency ranges. Some embodiments provide that the GPR is a non ground-coupled antenna that may include a horn antenna and/or an array antenna.

In some embodiments, the first and/or second sensor 22, 26 is a non-invasive sensor relative to the surface of the soil area. For example, some embodiments provide that the first and/or second sensor 22, 26 are configured to provide data without directly contacting the corresponding soil area. Some embodiments provide the first and/or second sensor 22, 26 is configured to move in a range from at the surface of the soil area to about six feet above the surface of the soil area.

Some embodiments further include a sensor support that is configured to physically support the first and/or second sensor 22, 26 and to be propelled across the surface of the soil area by the vehicle 20.

In some embodiments, the location associated data includes location associated soil compaction data that includes elevation data corresponding to soil compaction.

In some embodiments, the vehicle 20 is a self-driving vehicle and is configured to traverse the soil area in a path that is defined by a coverage plan that is based on the geographic location data. Some embodiments provide that the vehicle 20 is an airborne vehicle and is configured to fly over the soil area based on self-generated lift. In some embodiments, the airborne vehicle is configured to fly over the soil area in a pattern that is defined by a coverage plan that is based on the geographic location data.

In some embodiments, processing circuit is further configured to generate a tillage prescription plan for the soil area that is based on location associated soil compaction data. Some embodiments provide that the tillage prescription plan includes data that identifies a first portion of soil area not to till and a second portion of the soil area to till. In some embodiments, the tillage prescription plan includes data that identifies multiple portions of the soil area that each correspond to a different tilling depth. In some embodiments, the tillage prescription plan includes three-dimensional tillage data that defines a location corresponding to a portion of the soil area and a tilling depth that corresponds to the location. Some embodiments provide that the first and/or second sensor 22, 26 are non-invasive sensor(s). In some embodiments, the three-dimensional tillage data is graphically represented based on data generated using the non-invasive sensor.

Some embodiments provide that the processing circuit is further configured to transmit tillage prescription data to a tilling vehicle that includes a tilling implement. The tilling vehicle and/or the tilling implement are configured to implement the tillage prescription plan by varying tillage depth based on a tilling location. In some embodiments, the tilling implement is propelled by the tilling vehicle 20 and the tilling implement varies the tilling depth. For example, the tilling implement may be pushed and/or pulled by the tilling vehicle 20. Some embodiments provide that the tilling implement is mounted to the tilling vehicle and the tilling implement varies the tilling depth relative to the tilling vehicle 20.

In some embodiments, the tillage prescription plan is implemented automatically by the tilling vehicle 20 using the tilling implement. In some embodiments, the tilling implement includes multiple tilling implement elements that may be operated to till at different depths simultaneously based on the tillage prescription. In some embodiments, the tillage prescription data is transmitted to tilling vehicle in substantially real-time relative to generation of the location associated soil compaction data.

In some embodiments, the first and/or second sensor 22, 26 is located on a front of the vehicle 20 and is configured to generate the data corresponding to the soil area in the front of the vehicle 20. In such embodiments, the vehicle includes a tilling implement that is at a rear portion of the vehicle 20 and that is configured to vary the tilling depth of the soil area behind the vehicle 20. Some embodiments provide that the first and/or second sensor 22, 26 are at the front or rear of the vehicle 20 and the tilling implement is also at the front or rear of the vehicle proximate the sensor(s) 22, 26.

In some embodiments, the processing circuit includes a first processing circuit that is located on the vehicle 20 and a second processing circuit that is remote from the vehicle 20. For example, the first processing circuit may be configured to generate the location associated soil compaction data and to transmit the location associated compaction data to a data repository that is accessible by the second processing circuit and/or directly to the second processing circuit. In some embodiments, the processing circuit is configured to receive the location associated soil compaction data and to generate a tillage prescription plan for the soil area that is based on the location associated soil compaction data. In some embodiments, the second processing circuit is further configured to transmit the tillage prescription plan to a tilling vehicle 20.

Some embodiments provide that the processing circuit is further configured to generate the location associated physical, chemical and/or biological characteristic data of the soil and to generate a tillage prescription plan for the soil area that is based on the location associated physical, chemical and/or biological characteristic data. In some embodiments, the vehicle 20 includes the tilling implement and the processing circuit is further configured to cause the tilling implement to perform the tillage prescription plan.

In some embodiments, the first and/or second sensor 22, 26 provide that the first sensor uses a first sensor technology and the second sensor uses a second sensor technology that is different from the first sensor technology. In some embodiments, the first sensor technology is one of GPR, seismic, acoustic, laser and electromagnetic induction technologies and the second sensor technology is one of GPR, seismic, acoustic, laser and/or electromagnetic induction technologies that is different than the first sensor type. In some embodiments, the soil compaction data from the first sensor and the soil compaction data from the second sensor are used to generate composite location associated soil compaction data. Some embodiments provide that the processing circuit is further configured to generate location data corresponding to the vehicle based on the location associated soil compaction data.

Figure 9:
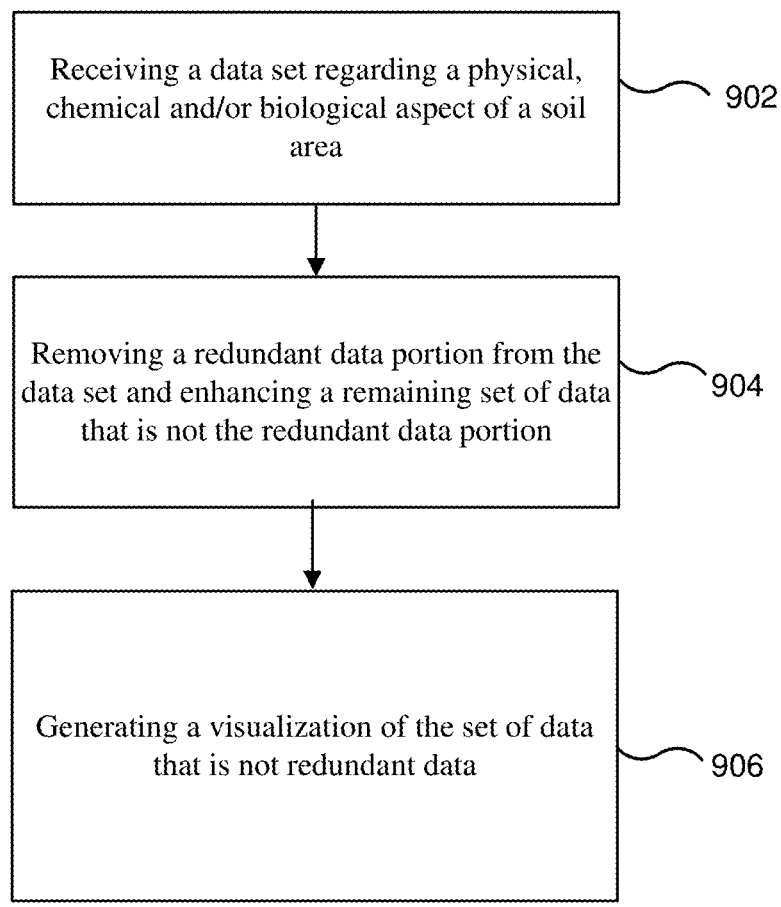
FIG. 9 is a flowchart of operations according to some embodiments herein.

Reference is now made to FIG. 9, which is a flowchart of operations according to some embodiments herein. Operations include receiving, using a processing circuit and from a sensor, a data set regarding a physical, chemical and/or biological aspect of a soil area (block 902). In some embodiments, the sensor is a ground penetrating radar and some embodiments provide that the sensor includes an electromagnetic induction device. Some embodiments provide that sensor includes a seismic transmission device.

Some embodiments provide that operations may include removing a redundant data portion from the data set using the processing circuit (block 904). Some embodiments provide that the processing circuit enhances a remaining set of data that is not the redundant data portion by removing the redundant data portion.

Operations may include generating a visualization of the set of data that is not redundant data (block 906). In some embodiments, the data that is not redundant data provides a data set reflecting a soil compaction measurement within the soil area. Some embodiments provide that the soil area is not deeper than 36 inches from a surface of the soil area.

In some embodiments, the visualization of the set of data determines a tillage program. Some embodiments provide that the measurement of soil compaction is used to determine a soil tillage prescription.

In some embodiments, the data set regarding the physical, chemical and/or biological aspect of the soil is analyzed with a neural network. Some embodiments provide that the neural network includes a training set that includes a data set regarding the soil area. The data set may include weather, physical, chemical, structural, topographical, and/or geographical data. The neural network may provide a visualization of the data set that depicts the bulk density of the soil area. The visualization of the data set may be displayed in at least two dimensions. The neural network may further provide a prescription for tilling the soil area based on the visualization of the data set.

Some embodiments provide that the two dimensions may include depth and density of the soil area and the visualization may include at least one other dimension.

Figure 10:
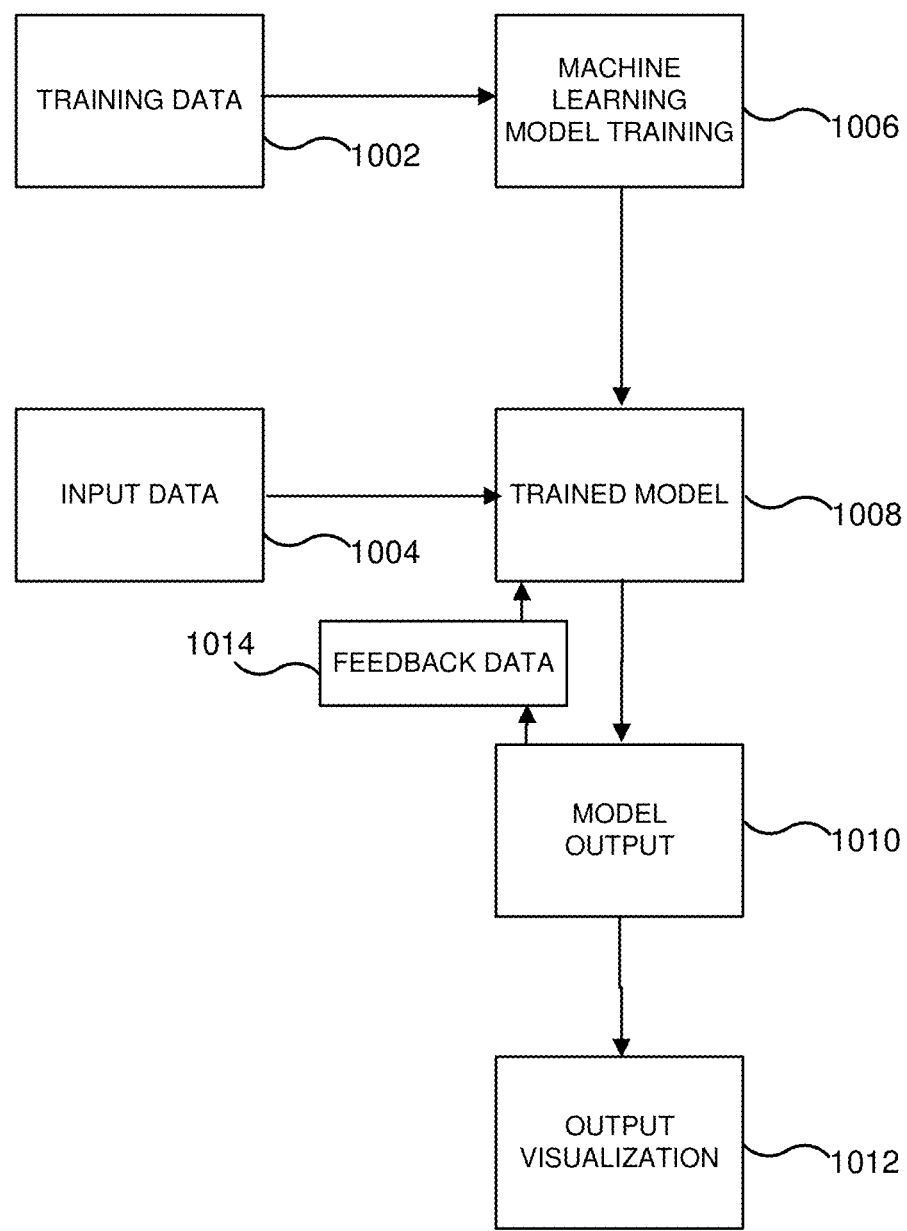
FIG. 10 is a flowchart of operations for training and using a machine learning model for operations according to some embodiments disclosed herein.

Reference is now made to FIG. 10, which is a flowchart of operations for training and using a machine learning model for operations according to some embodiments disclosed herein. Some embodiments provide that training data (block 1002) is provided to a machine learning platform as disclosed herein. The machine learning platform may perform machine learning model training using the training data that is provided (block 1006). The training data may include penetrometer curves, ground penetrating radar (GPR) scans and/or electromagnetic interference (EMI) scans, among others. The training data values may all be georeferenced according to some embodiments herein. In some embodiments, training data may include air and/or ground temperature, volumetric moisture content, digital elevation model images, soil probe results, penetrometer readings, core samples, acoustic in-situ measurements, in-situ ultrasound measurements, and/or excavation analysis, among others.

The machine learning model may be trained using any of the techniques described herein, including, for example, random forest, among others. The result of the training may include a trained machine learning model (block 1008).

Once the machine learning model is trained, input data 1004 may be provided to the model, which may generate model output data 1010. The input data 1004 may include GPR and EMI scans and the trained model 1008 may predict a penetrometer reading at each inch down to a given depth for every location that includes the scanned data. In some embodiments, the given depth may be about 12 inches, about 18 inches, about 24 inches, and/or about 36 inches, among others. The model output data 1010 may include predicted and/or estimated penetrometer curves that may be used to understand soil density and the presence of compacted layers thereof. In some embodiments, a compaction threshold may be determined and any values in the predicted penetrometer data that are above the compaction threshold may be designated for tillage while compaction values that are below the compaction threshold may not be designated for tillage.

The model output data 1010 may be used to generate an output visualization (block 1012). For example, the values that are above the compaction threshold that are designated for tillage may be marked as red while the values that are not above the compaction threshold may be marked with a color other than red in the visualization.

In some embodiments, the model output data 1010 may be used as feedback 1014 that may be provided to the trained model 1008 to increase the performance of the trained model 1008.

Figure 11:
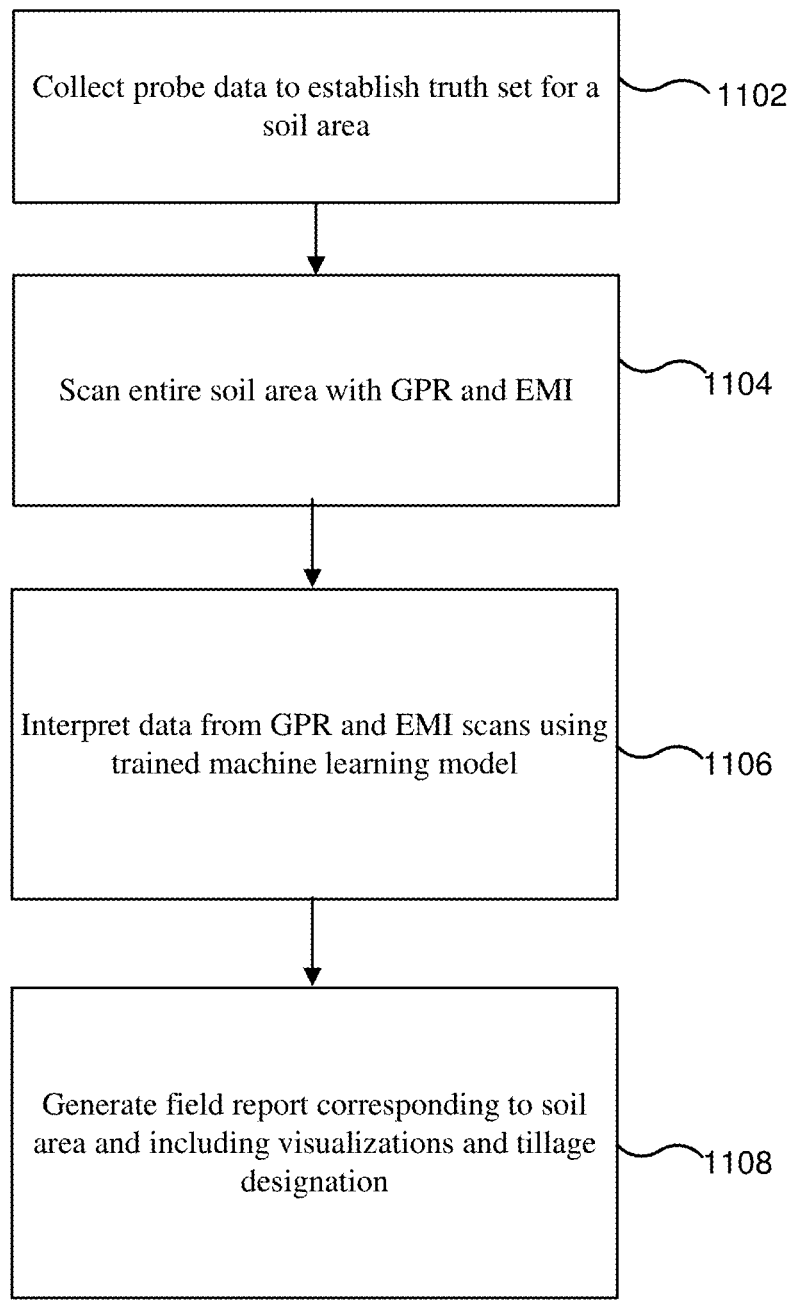
FIG. 11 is a flowchart of operations according to some embodiments herein.

Reference is now made to FIG. 11, which is a flowchart of operations according to some embodiments herein. As provided herein, systems may perform operations of collecting probe data to establish a truth set for a soil area (block 1102). Some embodiments provide that the soil area may be an agricultural field and/or a designated portion thereof. The soil area may be scanned with one or more sensors that are configured to use GPR and/or EMI (block 1104). The data from the GPR and EMI scans is interpreted using a trained machine learning model (block 1106). A field report is generated that corresponds to the soil area and that may include visualizations that are configured to communicate tillage designations.

Further Definitions and Embodiments

In the above-description of various embodiments of the present disclosure, aspects of the present disclosure may be illustrated and described herein in any of a number of patentable classes or contexts including any new and useful process, machine, manufacture, or composition of matter, or any new and useful improvement thereof. Accordingly, aspects of the present disclosure may be implemented in entirely hardware, entirely software (including firmware, resident software, micro-code, etc.) or combining software and hardware implementation that may all generally be referred to herein as a "circuit," "module," "component," or "system." Furthermore, aspects of the present disclosure may take the form of a computer program product comprising one or more computer readable media having computer readable program code embodied thereon.

Any combination of one or more computer readable media may be used. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable signal medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable instruction execution apparatus, create a mechanism for implementing the functions/acts specified in the flowchart and/or block diagram block or blocks.

These computer program instructions may also be stored in a computer readable medium that when executed can direct a computer, other programmable data processing apparatus, or other devices to function in a particular manner, such that the instructions when stored in the computer readable medium produce an article of manufacture including instructions which when executed, cause a computer to implement the function/act specified in the flowchart and/or block diagram block or blocks. The computer program instructions may also be loaded onto a computer, other programmable instruction execution apparatus, or other devices to cause a series of operational steps to be performed on the computer, other programmable apparatuses or other devices to produce a computer implemented process such that the instructions which execute on the computer or other programmable apparatus provide processes for implementing the functions/acts specified in the flowchart and/or block diagram block or blocks.

It is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

The flowchart and block diagrams in the figures illustrate the architecture, functionality, and operation of possible implementations of systems, methods, and computer program products according to various aspects of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular aspects only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Like reference numbers signify like elements throughout the description of the figures.

The corresponding structures, materials, acts, and equivalents of any means or step plus function elements in the claims below are intended to include any disclosed structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The aspects of the disclosure herein were chosen and described in order to best explain the principles of the disclosure and the practical application, and to enable others of ordinary skill in the art to understand the disclosure with various modifications as are suited to the particular use contemplated.

The invention claimed is:

1. A method comprising:
    traversing a soil area by a vehicle, the vehicle comprising an above ground sensor, a location device configured to provide location data related to the vehicle, and a processor in communication with the sensor and the location device;
    using the sensor, generating a data set relating to a physical, chemical and/or biological characteristic of the soil corresponding at soil locations while traversing the soil area;
    transmitting the data set to the processor;
    generating a tillage plan in real time or in near real time using a trained machine learning model to predict soil compaction, wherein the model was generated from a training set that comprises a soil data set comprising weather, physical, chemical, structural, topographical and/or geographical data, wherein the tillage plan reflects soil compaction measurements at the soil locations.

2. The method of claim 1, wherein the sensor is a ground penetrating radar.

3. The method of claim 1, wherein the sensor comprises a ground penetrating radar and an electromagnetic induction device.

4. The method of claim 1, wherein the sensor comprises a ground penetrating radar and a seismic transmission device.

5. A tillage vehicle comprising:
    a vehicle that is configured to travel over a soil area;
    a tilling implement that is configured to implement a tilling prescription plan that identifies tilling depths corresponding to different areas of the soil areas at a rear of the vehicle;
    a location device that is configured to provide location data corresponding to the tillage vehicle;
    at least one above ground sensor connected to the vehicle, the at least one above ground sensor configured to move above a surface of the soil area as the vehicle travels thereon and to generate data relating to a physical, chemical and/or biological characteristic of the soil corresponding to the soil area; and
    a processing circuit that is communicatively coupled to the at least one sensor, to the location device, and to the tillage implement and that is configured to receive the location data and the data relating to the physical, chemical and/or biological characteristic of the soil, and to generate, in real time or in near real time, the tilling prescription plan for use by the tilling implement based on the data relating to the physical, chemical and/or biological characteristic of the soil, wherein generating the tilling prescription plan comprises using a trained machine learning model, the model created using a training set that comprises a soil data set comprising weather, physical, chemical, structural, topographical and/or geographical data to predict soil compaction, wherein the at least one sensor is located forward of the tilling implement and is configured to generate the data corresponding to the soil area in the front of the vehicle, and wherein the tilling implement that is located rearward of the sensor and is configured to vary the tilling depth of the soil area behind the vehicle according to the tilling prescription plan generated by the processing circuit based on the data corresponding to the soil area generated by the at least one sensor on the front of the vehicle.

6. A processing device, comprising:

a processing circuit; and a memory that is coupled to the processing circuit and that includes instructions that, when executed by the processing circuit, causes the processing circuit to:

receive, from a location device, location data corresponding to a location of the processing circuit;

receive, from an above ground sensor that is proximate the processing circuit, data relating to a physical, chemical and/or biological characteristic of a soil area;

generate location associated data that relates the location data to the physical, chemical and/or biological characteristic of the soil area at respective locations corresponding to the location data;

using a trained machine learning model to generate, in real time or in near real time, a tillage prescription plan for the soil area that is based on location associated soil compaction data, the tillage prescription plan comprising three-dimensional tillage data that defines a location corresponding to a portion of the soil area and a tilling depth that corresponds to the location, wherein the trained machine learning model was created using a training set that comprises a soil data set comprising weather, physical, chemical, structural, topographical and/or geographical data to predict soil compaction.

7. The processing device of claim 6, wherein the data relating to the physical, chemical and/or biological characteristic of the soil correlates to a degree of soil compaction.

8. The processing device of claim 6, wherein the soil area comprises a plurality of soil area elements, wherein each soil area element corresponds to a specific geographic location and a corresponding location associated soil compaction data value.

9. The processing device of claim 6, wherein the sensor comprises a non-invasive sensor relative to the surface of the soil area.

10. The processing device of claim 6, wherein the location associated data comprises location associated soil compaction data that comprises elevation data corresponding to soil compaction.

11. The processing device of claim 6, wherein the processing circuit is on a vehicle, and wherein the vehicle comprises an airborne vehicle and is configured to fly over the soil area based on self-generated lift.

12. The processing device of claim 11, wherein the airborne vehicle is configured to fly over the soil area in a pattern that is defined by a coverage plan that is based on the location data.

13. The processing device of claim 6, wherein the processing circuit is further configured to transmit tillage prescription data to a tilling vehicle that includes a tilling implement, wherein the tilling vehicle and/or the tilling implement are configured to implement the tillage prescription plan by varying tillage depth based on a tilling location.

14. The processing device of claim 6, wherein the processing circuit is further configured to generate the location associated physical, chemical and/or biological characteristic data of the soil and to generate a tillage prescription plan for the soil area that is based on the location associated physical, chemical and/or biological characteristic data.

15. The processing device of claim 6, wherein the sensor comprises a plurality of sensors that includes a first sensor that comprises a first sensor technology and a second sensor that comprises a second sensor technology that is different from the first sensor technology.

16. The processing device of claim 6, wherein the physical, chemical and/or biological characteristic of the soil area comprises soil tilth.

17. The processing device of claim 6, wherein the physical, chemical and/or biological characteristic of the soil area comprises soil aggregate stability.

18. The method of claim 1 further comprising:

transmitting the tillage plan from the processor to the tilling implement; and implementing the tillage plan by tilling the soil at varying tillage depth based on the soil locations while traversing the soil area.

* * * * *